United States Patent [19]

Stüeber et al.

[11] Patent Number: 5,202,416
[45] Date of Patent: Apr. 13, 1993

[54] PROTEASE ABSORBENT FOR ISOLATING AND PURIFYING PROTEASES, A PROCESS FOR THE PREPARATION THEREFOR, AND THE METHOD FOR PURIFYING A PROTEASE

[75] Inventors: Werner Stüeber, Lahntal; Eric P. Pâques, Marburg, both of Fed. Rep. of Germany

[73] Assignee: Behringwerke Aktiengesellschaft, Marburg/Lahn, Fed. Rep. of Germany

[21] Appl. No.: 392,072

[22] Filed: Aug. 10, 1989

[30] Foreign Application Priority Data

Aug. 12, 1988 [DE] Fed. Rep. of Germany ....... 3827415

[51] Int. Cl.⁵ .................... A61K 37/02; C07K 5/08
[52] U.S. Cl. .................................. 530/322; 530/331
[58] Field of Search ............................. 530/322, 331

[56] References Cited

FOREIGN PATENT DOCUMENTS 0167152 1/1986 European Pat. Off. .

OTHER PUBLICATIONS

Stuerzebecher et al., Pharmazie, vol. 42 (1987).
Structures and Synthesis of Leupeptins Pr-LL and Ac-LL, Kawamura et al., Chem. Pharm. Bull., vol. 17, No. 9, pp. 1902-1909 (1969).
Synthesis of a Tripeptide with a C-terminal Nitrile Moiety and the Inhibition of Proteinases, Stuber et al., Int. J. Peptide Protein Res., vol. 31, pp. 63-70 (1988).

Primary Examiner—Merrell C. Cashion, Jr.
Assistant Examiner—S. G. Marshall
Attorney, Agent, or Firm—Finnegan, Henderson, Farabow, Garrett & Dunner

[57] ABSTRACT

Peptide derivatives of the Formula I

R—Y—Leu—Pro—NH—CH(CH$_2$—CH$_2$—CH$_2$—NH—C(=NH)—NH$_2$)—X in which Y is HN—(CH$_2$)$_n$—CO with n=1 to 8 or a bond, X is CN, CH$_2$OH or CHO and R is a support or a hydrogen atom, a process for the preparation thereof, and the use thereof for affinity chromatography, especially for isolating and purifying proteases, are described.

5 Claims, No Drawings

PROTEASE ABSORBENT FOR ISOLATING AND PURIFYING PROTEASES, A PROCESS FOR THE PREPARATION THEREFOR, AND THE METHOD FOR PURIFYING A PROTEASE

The invention relates to peptide derivatives of the Formula I

in which Y is HN—$(CH_2)_n$—CO with n=1 to 8 or a bond, X is CN, $CH_2OH$ or CHO and R is a support matrix suitable for affinity chromatography or is a hydrogen atom, to a process for the preparation thereof and to the use thereof for affinity chromatography, in particular for isolating and purifying proteases.

The isolation of proteases has been considerably improved in recent years by the technique of affinity chromatography. This method makes use of specific interactions between substances. It entails a substance being covalently bonded as ligand to an insoluble support (matrix). The ligand must be able to enter into a complex-like interaction with the substance which is to be isolated. The only substances retained by the ligand are those which react specifically with it. Other substances are washed out. The retained substances can be eluted from the support material using a solution of unbound ligand or, for example, with a salt gradient.

It is of course most beneficial for the isolation of a protein to use a ligand which enters into interactions only with one or a few proteins. The capacity of the adsorbent depends on the loading of the matrix with ligands being at a sufficiently high level. The chemical bonding should be as uniform and stable as possible, that is to say difficult to hydrolyze. Affinity chromatography can be employed, in particular, for obtaining proteases, for example from plasma, serum, body fluids, cells or cell culture supernatants. Affinity materials which have proven useful for this are immobilized inhibitors which are naturally occurring or prepared by synthesis. However, the use of the affinity materials described to date is, by reason of the inhibitors employed, limited by considerable deficiencies.

Low molecular weight inhibitors such as arginine or benzamidine do not have a sufficiently high inhibitory activity for affinity chromatography. Accordingly, large amounts of resin are required because of the low capacity. In contrast with this, polypeptide inhibitors such as aprotinin, SBTI, BPTI, hirudin or eglin have too strong an inhibitory effect so that the protease bound to the affinity resin can be eluted only under extreme conditions and/or with a considerable loss in yield.

The present invention had the object of preparing a material for affinity chromatography which has a high capacity, ligand density and stability and can be employed for isolating proteinases.

EP-A 0167152 describes the peptide derivative D-Val-Gly-DL-arginal bound to a support as affinity material. However, this material is not optimal and results, as indicated in the examples in this application, in losses in yield at the level of about 30%.

It has now been found, surprisingly, that this disadvantage can be eliminated by replacing the Val-Gly-arginal sequence by the sequences Leu-Pro-arginal, D-Leu-Pro-arginal, L-Leu-Pro-DL-arginal or DL-Leu-Pro-DL-arginal. It is likewise possible to replace the aldehyde derivative arginal by a corresponding nitrile derivative or alcohol derivative.

Hence the invention relates to a compound of the following Formula I:

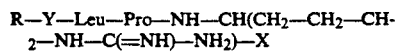

in which Y is HN—$(CH_2)_n$—CO with n=1 to 8 or a bond,
X is CN, $CH_2OH$ or CHO and
R is a support matrix suitable for affinity chromatography or is a hydrogen atom.

If R denotes a support, the support is preferably a polymer which has a carbohydrate-based structure or a structure based on methacrylamide, N-methylene-bis-methacrylamide, glycidyl methacrylate-polyethylene glycol derivatives and pentaerythritol dimethacrylate, especially ®SEPHAROSE, ®BIOGEL, ®SEPHADEX, ®CELLEX or ®FRACTOGEL.

The invention also relates to a process for a preparation of a compound of the Formula I, which comprises protected amino acids or peptide segments being built up by methods known per se to give the corresponding peptides, with the C-terminus of arginine being converted into an alcohol, aldehyde or nitrile functionality and, where appropriate, this peptide being bonded to a polymer after elimination of the protective groups.

To prepare a compound according to the invention, which has at the C-terminal end an alcohol group or aldehyde group, by a process known per se, the synthesis is preferably started with an arginine ester, preferably a methyl or ethyl ester, whose guanidino group can be blocked with a protective group customarily used in peptide chemistry, but is preferably protected by protonation, entailing repetitive coupling of individual protected amino acid derivatives, preferably a protected peptide segment, to the N-alpha group of the arginine derivative, with purification of the intermediates. These peptide segments have the structures P—Y—Leu—Pro—OH, where P is a protective group, preferably Boc, and Y has the meaning indicated above. Leucine is in the D, L or DL, but preferably in the D, form and proline is in the L form. The synthesis is carried out in solution by reacting a proline ester, preferably the methyl or benzyl ester, with a leucine derivative protected at the N terminus, with the Boc group preferably acting as protective group, to form a dipeptide. Suitable and preferred solvents are dimethylformamide, dimethyl sulfoxide, dichloromethane, choroform, N-methylpyrrolidone and mixtures thereof. The formation of the peptide linkage is achieved by activating the carboxyl group, for which purpose the activation methods customarily used in peptide chemistry are suitable, preferably the active ester method and, particularly preferably, the carbodiimide method with the addition of HOBt and, where appropriate, a base, preferably N-methylmorpholine. The peptides are purified by extraction from aqueous solution using a solvent which has a low solubility in water, preferably with ethyl acetate.

The N-terminal protective group is removed where appropriate, and the same method is used to couple Boc—protected Y—OH, where Y—OH is preferably epsilon-aminocaproic acid, to the dipeptide. The ester group on the proline is removed by hydrolysis or hydrogenolysis. The reaction for the segment coupling to the arginine derivative is preferably carried out in accordance with the preparation of the dipeptide. The dipeptide derivative is then dissolved in an alcohol, preferably ethanol, and reduced with sodium borohydride in the presence of $CaCl_2$. A preferred embodiment of this reduction entails dissolving 20 g of Boc—Aca—D—Leu—Pro—Arg—OMe in 200-500 ml ethanol, dissolving in this 7-15 g of $CaCl_2.2H_2O$, preferably 11 g, and reducing the methyl ester with 5-10 g, preferably 6.5 g, of sodium borohydride. The reaction temperature is maintained in the range from 4° to 50° C. for 30 min to 6 hours, preferably at room temperature for 1 hour. The reduced peptide is obtained from the aqueous phase by extraction with a water-immiscible solvent, preferably butanol. Protective groups present at this stage are removed where appropriate, preferably by acidolysis.

The arginal derivatives according to the invention are preferably prepared by partial oxidation of the corresponding arginol derivatives, as is described in Chem. Pharm. Bull. 17 (9), 1902-1909 (1969).

In a preferred embodiment of this oxidation, 5 g of Boc—Aca—D—Leu—Pro—Arg—OH are dissolved in 80-120 ml of dimethyl sulfoxide and reacted with 6-12 g, preferably 8 g, of dicyclohexylcarbodiimide, and 500 mg-1500 mg, preferably 850 mg, of anhydrous crystalline orthophosphoric acid. The reaction time is 6-24 hours, preferably 14 hours, at room temperature. The crude peptide is chromatographed on ®SEPHADEX 20 in methanol.

The Boc protective group which is preferably employed at the N terminus is then removed, where appropriate, by acidolysis, preferably with a mixture of 50% trifluoroacetic acid, 45% methylene chloride and 5% anisole. The preparation of a peptide which has a peptide sequence according to the invention and whose C-terminal group has a cyano group is preferably likewise carried out using the abovementioned peptide segments of the general structure P—Y—Leu—Pro—OH in which P is a protective group, preferably Fmoc, and Y is a bond or NH—$(CH_2)_n$—CO with n=1 to 8, preferably n=6.

Arg—CN is used as C-terminal building block, and its preparation is described in Int. J. Pept. Prot. Res. 31, 63-70 (1988).

The N-terminal protective group, preferably Fmoc, is eliminated with a base, preferably 20% piperidine in DMF, and the peptide nitrile is purified by chromatography on ®SEPHADEX LH 20.

The peptides according to the invention are distinguished by a strong inhibitory action on t-PA. In addition, these peptides are, surprisingly, suitable for the affinity chromatography of t-PA when these peptides are bonded to a polymer which is brought into contact with a solution containing t-PA. It was very particularly surprising that immobilized peptides with a group Y, as described above, with n preferably=6, had a distinctly higher binding affinity to t-PA than those immobilized peptides in which Y is a bond.

The invention also relates to the use of these peptides for purifying proteases, preferably serine and cysteine proteases, particularly preferably tissue plasminogen activator, prourokinase, urokinase, and the derivatives thereof which are naturally occurring or prepared by synthesis or genetic manipulation, from plasma, serum, body fluids, cells or cell culture supernatants.

A process for purifying proteases preferably comprises bringing the starting material with a conductivity of 0 to 100 mSi and a pH of 3 to 11, preferably with a conductivity of 0 to 30 mSi and a pH of 5 to 8, into contact with the affinity material. The material is washed with a buffered solution (pH 3 to 11; conductivity 0 to 100 mSi, preferably pH 4 to 8 and conductivity 0 to 30 mSi), and then the protease is eluted with a buffered neutral salt solution. It is possible in this way for proteases which enter into an interaction with the peptide sequence of the compounds of the Formula I to be adsorbed from solutions and, where appropriate, then eluted, for example t-PA, prourokinase and urokinase. When an affinity material prepared by the described method was used, it emerged that the binding capacity was higher and the recovery rate was over 90% instead of 75% for t-PA by comparison with a material which was prepared as described in EP-A 0 167 152 from Val-Gly-arginal and an insoluble support material.

Abbreviations

SBTI: Soybean trypsin inhibitor
BPTI: Bovine pancreas trypsin inhibitor
DMF: Dimethylformamide
Fmoc: 9-Fluorenylmethyloxycarbonyl
Boc: Butyloxycarbonyl
HOBt: Hydroxybenzotriazole
Arg: Arginine
Pro: Proline
Leu: Leucine
Gly: Glycine
Val: Valine
t-PA: Tissue plasminogen activator
mSi: Millisiemens
DCC: Dicyclohexylcarbodiimide
DCU: Dicyclohexylurea
Z: Benzyloxycarbonyl Chiral amino acids may be in the D or L form. Where no specification is made, the L form is meant.

EXAMPLES

Example 1

Preparation of D-Leu-Pro-arginol 4.3 g of Boc-Pro, 2.7 g of HOBt and 4.2 g of DCC were dissolved in 50 ml of DMF and, after 1 hour, 5.22 g of arginine methyl ester dihydrochloride and 2.2 ml of N-methylmorpholine were added. The mixture was stirred at room temperature overnight, DCU was filtered off, and the solvent was evaporated off in vacuo. The residue was dissolved in ethyl acetate, the solution was extracted several times with water, and the aqueous phase was freeze-dried. The crude product was dissolved in n-butanol and extracted three times with water. The organic phase was dried over sodium sulfate and then the solvent was evaporated off. 7.1 g of Boc-Pro-Arg-OMe were treated with 150 ml of 1.2N HCl/glacial acetic acid at room temperature for 1 hour, and the eliminating agent was distilled off in vacuo. The oily residue was dried and then 4 g of Boc-D-Leu were activated with 2.4 g of HOBt and 3.64 g of DCC in 50 ml of DMF for 1 hour and added to the dipeptide. After 1.9 ml of N-methylmorpholine had been added, the reaction mixture was stirred at room temperature overnight, insolubles were removed by filtration, and the solvent was evaporated off. The oily residue was partitioned between ethyl acetate and water, the ethyl acetate phase was then extracted twice with small portions of water, and the aqueous phase was freeze-dried. The crude product was chromatographed on ®SEPHADEX-LH 20 in methanol (yield 5.8 g). 1.95 g of this methyl ester derivative and 2.16 g of $CaCl_2.2H_2O$ were dissolved in 100 ml of ethanol at room temperature, and 0.8 g of sodium borohydride was added in 4 portions each of 200 mg. After 1 hour the solvent was evaporated off, the residue was taken up in a little water, and the product was extracted with butanol. The butanol solution was dried with sodium sulfate and then the solvent was evaporated off and the residue was chromatographed on 20 in methanol (yield 1.12 g).

1 g of Boc—D—Leu—Pro—Arg—$CH_2OH$ was dissolved in 50 ml of trifluoro acetic acid/dichloromethane/anisole (45:50:5) and stirred at room temperature for 15 min. The solvent was then evaporated off in vacuo, the residue was taken up in water, the solution was extracted twice with diethyl ether, and the aqueous phase was freeze-dried (yield 835 mg).

Amino acid analysis: Leu 1.00; Pro 1.04; Arg 0.04.

Example 2

Preparation of
epsilon—Aca—D—Leu—Pro—Arg—CHO 9.3 g of Boc-epsilon-Aca, 5.4 g of HOBt and 8.4 g of DCC were stirred in 100 ml of DMF for 1 hour. Then 19 g of D-Leu-Pro-Arg-OMe×2 HCl (for preparation, see Example 1: the Boc group was eliminated from Boc—D—Leu—Pro—Arg—OMe with 1.2N HCl/glacial acetic acid) and 4.4 ml of N-methylmorpholine were added, and the mixture was stirred overnight. Insolubles were filtered off, the solvent was distilled off, and the residue was taken up in water. The aqueous phase was extracted by shaking twice with ethyl acetate and was freeze-dried. The crude product was dissolved in upper phase (500 ml of water, 400 ml of n-butanol and 100 ml of glacial acetic acid mixed thoroughly and separated in a separating funnel; the resulting phases were used as upper/lower phase) and extracted several times with the lower phase. The upper phase was concentrated and crystallized with diethyl ether. 17.3 g of this product were dissolved in 400 ml of ethanol, and 10.3 g of $CaCl_2 \times 2 H_2O$ and 5.9 g, in portions, of sodium borohydride were added. The mixture was stirred at room temperature for 1 hour, and the solvent was then distilled off in vacuo. The residue was taken up in water and extracted several times with n-butanol. The organic phase was dried over sodium sulfate and concentrated in a rotary evaporator. 9.2 g of Boc—epsilon—Aca—D—Leu—Pro—Arg—$CH_2OH$ were dissolved in 200 ml of dimethyl sulfoxide and reacted with 13.95 g of DCC and 1.5 g of anhydrous phosphoric acid. After a reaction time of 4 hours at room temperature, the solvent was evaporated off in vacuo, the residue was taken up in methanol, and the solution was chromatographed on ®SEPHADEX-LH 20. 8.1 g of the Boc-protected aldehyde peptide were dissolved in 40 ml of dichloromethane, 4 ml of anisole and 40 ml of trifluoro acetic acid and stirred at room temperature for 15 min. The mixture was then crystallized by dropwise addition to diethyl ether, and the crystals were collected and dried under high vacuum (yield 8.0 g).

Example 3

Preparation of
epsilon—Aca—D—Leu—Pro—Arg—CN 8.6 g of proline tert.-butyl ester, 13.25 g of Z—D—leucine, 8 g of HOBt and 10.5 g of DCC were dissolved in 100 ml of DMF and stirred at room temperature overnight. Insolubles were filtered off and the solvent was distilled off in vacuo. The oily residue was dissolved in ethyl acetate and washed three times each with saturated sodium bicarbonate solution, 5% potassium bisulfate solution and saturated brine. The organic phase was dried over sodium sulfate, the solvent was removed, and the Z protective group was removed in methanol using Pd/C and hydrogen. The free amino groups were converted into the hydrochloride by addition of HCl/methanol. The solvent was removed and then Leu-Pro tert.-butyl ester was crystallized from methanol/diethyl ether. 12.2 g of this product were stirred with 8.1 g of HOBt, 14.1 g of Fmoc-Aca, 9.1 g of DCC and 4.4 ml of N-methylmorpholine in 150 ml of DMF at room temperature overnight. DCU was filtered off and then the product was precipitated by addition of water. The crystals were collected and dried over $P_4O_{10}$ under high vacuum. 19.4 g of the t-butyl ester were stirred with 150 ml of 1.2N HCl/glacial acetic acid at room temperature for 1 hour, and the eliminating agent was evaporated off in vacuo. The residue was recrystallized from methanol/diethyl ether. This product was stirred with 6.7 g of HOBt and 6.8 g of DCC in 150 ml of DMF at room temperature for 1 hour. The DCU was then removed and subsequently 12.25 g of Arg—CN×2 TFA (Int. J. Peptide Prot. Res. 31, 63 (1988)) and 3.8 ml of N-methylmorpholine were added. After stirring overnight, the solvent was evaporated off, and the crude product was chromatographed in portions on ®SEPHADEX-LH 20 in methanol. 13.2 g of Fmoc-epsilon-Aca-D-Leu-Pro-Arg-CN were stirred with 20% piperidine/DMF (V/V) at room temperature for 30 min and then the eliminating reagent was evaporated off in vacuo. The crude product was dissolved in methanol, acidified with HCl/methanol and crystallized by dropwise addition to diethyl ether (9.3 g).

Amino acid analysis: Aca 0.93; Leu 0.95; Pro 1.05; Arg 1.04

Example 4

Immobilization of the peptides on ®Sepharose activated with cyanogen bromide 10 g of ®SEPHADEX (Pharmacia) activated with cyanogen bromide were suspended in 100 ml of 0.001N HCl, washed with 500 ml of 0.001N HCl on a filter frit and then washed in portions with 500 ml of 0.25M sodium bicarbonate solution. 1.5 g of peptide from Example 2 or 3 were dissolved in 30 ml of 0.25M sodium bicarbonate solution and added to the resin. The mixture was shaken at 4° C. overnight, filtered with suction and washed with 500 ml of 0.1M sodium bicarbonate. The resin was incubated with 100 ml of 0.1 ethanolamine pH8 at room temperature for 2 hours and then washed 3×alternately with 600 ml of 0.1M sodium acetate solution pH 4 and 600 ml of 0.1M sodium bicarbonate pH 8.4. Finally, the resin was thoroughly washed with water.

Example 5

1. Starting solutions: (SM)

a) Supernatant of a t-PA-producing Bowes melanoma cell culture (Eur. J. Biochem. 132, 681–686, 1983)

b) Supernatant of a CHO cell culture which produces a deglycosylated t-PA molecule described in EP-A 0227 462 (mutant I)
c) Supernatant of a t-PA wild-type described in GB 2119804
d) Human urine after dialysis against 50 mM tris, 100 mM NaCl pH 7.0

2. Affinity resins: (R)

1. Sepharose-Aca-D-Leu-Pro-arginal (Examples 2/4)
2. Sepharose-Aca-D-Leu-Pro-argininonitrile (Examples 3/4)
3. Sepharose-L-Val-Gly-DL-arginal described in EP-A 0 167 152

3. Procedure:

2 g of affinity resin (1-3) were added in each case to 10 ml of each of the starting solutions (a-d) and incubated at RT for 30 min. The resin was then separated off, and the antigen concentration in the supernatant was determined by ELISA.

4. Results

| R | SM | | | |
|---|---|---|---|---|
| | a | b | c | d |
| 1 | 5% | 6% | 4% | 9% |
| 2 | 12% | 11% | 15% | 20% |
| 3 | 35% | 36% | 28% | 45% |

Example 6

10 l of solution b (Example 1) were incubated with 300 g of resin 1 (Example 1) at RT while stirring for 30 min. The mixture was packed into a column and washed with 5 l of a solution containing 0.1M NaCl, 50 mM glycine pH 7. t-PA was then eluted with a solution containing 0.5M arginine, 10 mM acetic acid pH 4.0. The yield was 98%.

We claim:
1. A peptide derivative of the Formula I

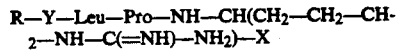

R—Y—Leu—Pro—NH—CH(CH$_2$—CH$_2$—CH$_2$—NH—C(=NH)—NH$_2$)—X in which Y is HN—(CH$_2$)$_n$—CO with n=1 to 8 or a bond,
X is CN, CH$_2$OH or CHO and
R is a support matrix suitable for affinity chromatography or is a hydrogen atom.
2. A peptide derivative as claimed in claim 1, wherein some or all of the optically active centers are in the L form.
3. A peptide derivative as claimed in claim 1, wherein the support matrix is a polymer.
4. A peptide derivative as claimed in claim 1, wherein the support is a polymer which has a carbohydrate-based structure or a structure based on methacrylamide, N-methylene-bis-methacrylamide, glycidyl methacrylate-polyethylene glycol derivatives or pentaerythritol dimethacrylate.
5. A peptide derivative as claimed in claim 1, wherein the support ®SEPHAROSE, ®BIOGEL, ®SEPHADEX, ®CELLEX or ®FRACTOGEL.

* * * * *

UNITED STATES PATENT AND TRADEMARK OFFICE
CERTIFICATE OF CORRECTION

PATENT NO. : 5,202,416
DATED : April 13, 1993
INVENTOR(S) : Stüber, et al

It is certified that error appears in the above-indentified patent and that said Letters Patent is hereby corrected as shown below:

On the title page, under item [19] and item [75], change "Stüeber" to --Stüber--.

On the title page, item [54] and column 1, line 2, change "ABSORBENT" to --ADSORBENT--.

Column 8, line 33, claim 5, after "support" insert --is--.

Signed and Sealed this

Twenty-seventh Day of December, 1994

Attest:

BRUCE LEHMAN

Attesting Officer     Commissioner of Patents and Trademarks